United States Patent
Tsuji et al.

(10) Patent No.: US 6,638,524 B2
(45) Date of Patent: Oct. 28, 2003

(54) COSMETICS, FOODS AND BEVERAGES SUPPLEMENTED WITH PURIFIED STRICTININ

(75) Inventors: Kenkou Tsuji, Shizuoka (JP); Mari Yamamoto, Shizuoka (JP); Keiko Kawamoto, Shizuoka (JP); Hirofumi Tachibana, Fukuoka (JP)

(73) Assignees: National Agricultural Research Organization, Tsukuba (JP); Bio-oriented Technology Research Advancement Institution, Omiya (JP)

( * ) Notice: Subject to any disclaimer, the term of this patent is extended or adjusted under 35 U.S.C. 154(b) by 0 days.

(21) Appl. No.: 10/131,211

(22) Filed: Apr. 25, 2002

(65) Prior Publication Data

US 2003/0003121 A1 Jan. 2, 2003

Related U.S. Application Data

(63) Continuation of application No. 09/778,820, filed on Feb. 8, 2001, now Pat. No. 6,491,943.

(30) Foreign Application Priority Data

Jun. 29, 2000 (JP) ......................... 2000-195672

(51) Int. Cl.$^7$ .......................... A61K 47/00; A61K 7/06; A61K 7/00
(52) U.S. Cl. .................... 424/439; 424/401; 424/70.1; 514/844; 514/845; 514/846; 514/847; 514/848
(58) Field of Search ................... 424/400, 401, 424/70.1, 439; 514/844, 845, 846, 847, 848

(56) References Cited

U.S. PATENT DOCUMENTS 6,264,995 B1    7/2001  Newmark et al.
6,280,715 B1 *  8/2001  Seguin et al. ............... 424/69

FOREIGN PATENT DOCUMENTS

JP    10072361 A    3/1998
JP    10218784 A    8/1998

OTHER PUBLICATIONS

Kashiwada Y, Nonaka G, Nishioka I, Chang JJ, Lee KH, Antiumor agents, 129. Tannins and related compounds as selective cytotoxic agents. Journal of Natural Products (Aug. 1992) 55 (8): 1033–43.*

Degenhardt, A., Engelhardt, U.H., Lakenbrink, C., Winterhalter, P., Preparation seperation of polyphenols from tea by high–speed countercurrent chromotography. Aug. 2000 Journal of Agric. F Chem. 48(8):3425–30.

Yang, de Villiers, McClain, Varilek, Green Tea polyphenols block endotoxin–induced tumor necrosis factor–production and lethality in a murine model. Dec. 1998 The Journal of Nutrition 128(12):2334–40.

Nonaka, G., et al., Hydrolyzable tannins and proanthocyanidins fron green tea. Phytochemistry 1984, 23, 1753–55.

* cited by examiner

Primary Examiner—Thurman K. Page
Assistant Examiner—Rachel M. Bennett
(74) Attorney, Agent, or Firm—Oblon, Spivak, McClelland, Maier & Neustadt, P.C.

(57) ABSTRACT

This invention is to provide an agent for therapy and prevention of allergic diseases which has no adverse action, shows a high safety even by administration for a long period and is able to be utilized to food and/or beverage, cosmetics, etc. which are used daily. To be specific, it provides anti-allergic agent and anti-inflammatory agent characterized in containing at least one polyphenol selected from strictinin and methylated derivatives thereof as an effective ingredient; a method for the addition of an antiallergic agent for oral administration or an anti-inflammatory agent for oral administration which is characterized in containing at least one polyphenol selected from strictinin and methylated derivatives thereof as an effective ingredient to food and/or beverage for prevention, suppression and mitigation of allergic symptoms or inflammatory symptoms.

28 Claims, 4 Drawing Sheets

```
              50 % ETHANOL FRACTION (Fr.1)
                         │
                 WATER-CHLOROFORM
                   ┌─────┴─────┐
            CHLOROFORM LAYER    AQUEOUS LAYER
                (Fr.2)              │
                              ETHYL ACETATE
                              ┌─────┴─────┐
                      ETHYL ACETATE LAYER   AQUEOUS LAYER
                           (Fr.3)              │
                                           n-BUTANOL
                                         ┌─────┴─────┐
                                  n-BUTANOL LAYER   AQUEOUS LAYER
                                      (Fr.4)          (Fr.5)
```

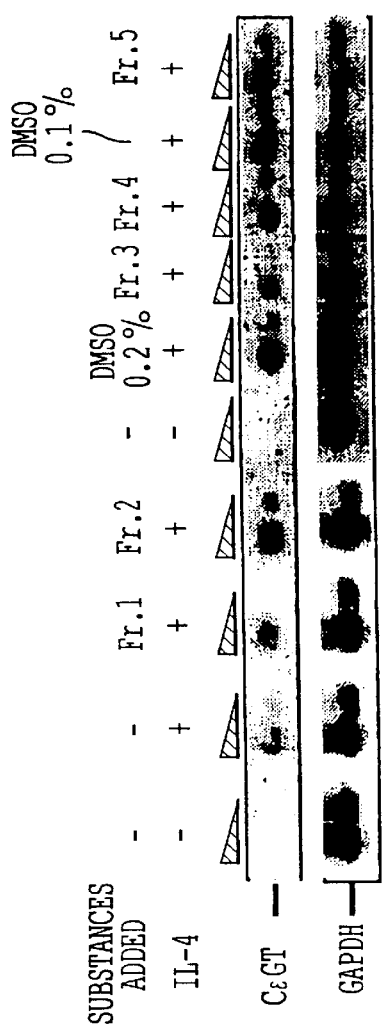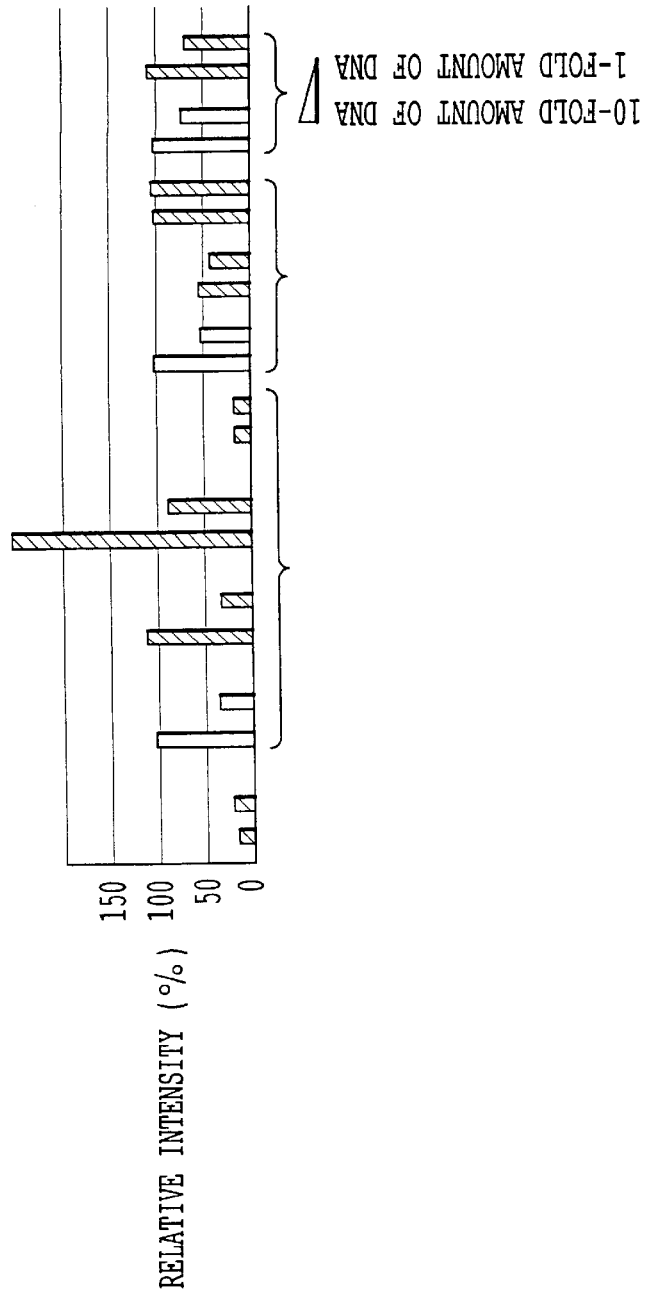

SEQUENCE LISTING

<160> NUMBER OF SEQ ID NOS: 5

<210> SEQ ID NO 1
<211> LENGTH: 25
<212> TYPE: DNA
<213> ORGANISM: ARTIFICIAL SEQUENCE
<220> FEATURE:
<223> OTHER INFORMATION: ARTIFICIAL DNA

<400> SEQUENCE: 1
aggctccact gcccggcaca gaaat                    25

<210> SEQ ID NO 2
<211> LENGTH: 25
<212> TYPE: DNA
<213> ORGANISM: ARTIFICIAL SEQUENCE
<220> FEATURE:
<223> OTHER INFORMATION: ARTIFICIAL DNA

<400> SEQUENCE: 2
acggaggtgg cattggaggg aatgt                    25

<210> SEQ ID NO 3

-continued

```
<211> LENGTH: 22
<212> TYPE: DNA
<213> ORGANISM: ARTIFICIAL SEQUENCE
<220> FEATURE:
<223> OTHER INFORMATION: ARTIFICIAL DNA

<400> SEQUENCE: 3
gctcagacac catggggaag gt                                              22

<210> SEQ ID NO 4
<211> LENGTH: 22
<212> TYPE: DNA
<213> ORGANISM: ARTIFICIAL SEQUENCE
<220> FEATURE:
<223> OTHER INFORMATION: ARTIFICIAL DNA

<400> SEQUENCE: 4
gtggtgcagg aggcattgct ga                                              22

<210> SEQ ID NO 5
<211> LENGTH: 25
<212> TYPE: DNA
<213> ORGANISM: ARTIFICIAL SEQUENCE
<220> FEATURE:
<223> OTHER INFORMATION: ARTIFICIAL DNA

<400> SEQUENCE: 5
agctgtccag gaacccgaca gggag                                           25
```

US 6,638,524 B2

COSMETICS, FOODS AND BEVERAGES SUPPLEMENTED WITH PURIFIED STRICTININ

This application is a Con of Ser. No. 09/778,820 filed Feb. 8, 2001, now U.S. Pat. No. 6,491,943.

FIELD OF THE INVENTION

The present invention relates to a pharmaceutical agent as well as food and/or beverage and cosmetics containing at least one polyphenol compound selected from strictinin and methylated derivatives thereof as an effective ingredient and, more particularly, it relates to a food having an action of suppressing the immediate-type and delayed-type allergy, to a pharmaceutical agent with an object of improving the allergy and to a cosmetic agent containing the same.

BACKGROUND OF THE INVENTION

In recent years, an increase in allergic diseases has been noted and it is reported that, in about one-third of the newborn babies, onset of atopic dermatitis or asthma is observed. A drastic increase in onset of pollinosis has been becoming a big social problem as well.

It has been believed that changes of environment surrounding us such as westernization of meals, air pollution, food additives and excessive stress are the causes of an increase in such allergic symptoms.

In view of the immunological competent cell and immunoglobulin which are participated therein, allergic reaction is classified into from type I to type IV. Diseases represented by allergic rhinitis and bronchial asthma belong to the allergic reaction of type I where IgE antibody is produced in large quantities when exposed to allergen and chemical mediators such as histamine, leukotrienes and prostaglandin are produced and released from mast cells and basophils via the said IgE antibody whereby dilation of blood vessel, promotion of blood vessel permeability, shrinking of bronchial smooth muscles, stimulation of nerve terminals, etc. are induced. Therefore, for the therapy of allergic diseases of type I, antihistaminic agents and antiallergic agents having an action of suppressing the liberation of chemical mediators from mast cells have been used.

However, antihistaminic agents and basic antiallergic agents have adverse actions such as drowsiness, thirst, gastrointestinal troubles, etc. and their continuous administration for a long period causes a problem.

Allergic reaction of type IV is a reaction of a delayed type in which T cells are participated where T cells receiving an antigen information via antigen-presenting cells such as Langerhans cells and macrophage produce and release various cytokines whereby an inflammation reaction of a delayed type takes place due to accumulation of eosinophils and macrophages.

Allergic contact dermatitis is a typical disease which occurs due to an allergic reaction of type IV. Steroid agents are used for the therapy of allergic diseases of type IV and such steroid agents suppress the production of cytokine in T cells and show a dramatic effect for the therapy of eczema. On the other hand however, there is a possibility that they cause severe adverse actions such as a decrease in adrenocortical function, flushing of the skin, atrophy and dilation of capillaries by their administration for a long period.

In the meanwhile, tea is a typical luxurious beverage and has been drunk by many people during more than 2000 years. It has been also known that tea has various physiological functions and, for example, its antioxidative action, antitumor action, suppressive action to carcinogenesis, antibacterial action, antiviral action and anticarious action have been reported.

With regard to an allergic action, there have been exemplified the therapeutic agent to the allergic reaction of type I as an antiallergic agent mainly comprising an extract from oolong tea using an action of suppressing the histamine liberation from mast cells as an indicator in Japanese Patent Laid-Open No. 258726/1991; the effective cases of natural caffeine for the promoting reaction of blood vessel permeability in allergic symptom of type I in Japanese Patent Laid-Open No. 17865/1995; and therapeutic agents such as antiallergic agent, anti-inflammatory agent, anti-atopic dermatitis agent and anti-psoriasis where an extract of oolong tea is an effective ingredient in Japanese Patent Laid-Open Nos. 77231/1998 and 175874/1998.

It has been further reported that green tea catechins such as epigallocatechin gallate and epicatechin gallate suppress the liberation of histamine from mast cells in abdominal cavity of rat (Journal of Japanese Society for Food Science and Technology, Vol. 42, No. 11, p. 952–958, 1955; and *Allergy*, Vol. 52, No. 1, pp. 58–64, 1997). However, there has been no report that polyphenols such as strictinin suppress the production of IgE by B cells which is an origin of allergic reaction.

Pharmaceutical agents for allergic diseases have been developed and used for the therapy already but, since they have adverse actions, there has been a strong demand for antiallergic agents derived from natural products where a long-term administration is possible, safety is high and no adverse reaction takes place.

Thus, an object of the invention is to provide a therapeutic and preventive agent for allergic diseases which has no adverse action, shows a high safety even by a long-term administration and is able to be utilized for food and/or beverage and cosmetic agent which are used daily.

In order to solve the above-mentioned problems, the present inventors have carried out a screening of substances having antiallergic action using a suppressive action for the production of IgE as an indication and have found that polyphenols such as strictinin exhibits such an effect and, based upon such a finding, the invention has been achieved.

SUMMARY OF THE INVENTION

The invention mentioned in claim 1 is an antiallergic agent which is characterized in containing, as an effective ingredient, at least one polyphenol selected from strictinin and methylated derivatives thereof.

The invention mentioned in claim 2 is an anti-inflammatory agent which is characterized in containing, as an effective ingredient, at least one polyphenol selected from strictinin and methylated derivatives thereof.

The invention mentioned in claim 3 is the antiallergic agent according to claim 1 wherein the antiallergic agent is that for oral administration.

The invention mentioned in claim 4 is the anti-inflammatory agent according to claim 2 wherein the anti-inflammatory agent is that for oral administration.

The invention mentioned in claim 5 is food and/or beverage containing an antiallergic agent for oral administration or an anti-inflammatory agent for oral administration which is characterized in containing, as an effective ingredient, at least one polyphenol selected from strictinin and methylated derivatives thereof.

The invention mentioned in claim 6 is a method for the addition of an antiallergic agent for oral administration or an anti-inflammatory agent for oral administration which is characterized in containing, as an effective ingredient, at least one polyphenol selected from strictinin and methylated derivatives thereof to food and/or beverage for prevention, suppression and mitigation of allergic symptoms or inflammatory symptoms.

The invention mentioned in claim 7 is a cosmetic agent containing an antiallergic agent for external use or an anti-inflammatory agent for external use which is characterized in containing, as an effective ingredient, at least one polyphenol selected from strictinin and methylated derivatives thereof.

BRIEF DESCRIPTION OF THE DRAWINGS

FIG. 2 shows an influence of each of the fractionated fractions on a CεGT-inducible expression by IL-4.

DETAILED DESCRIPTION OF THE INVENTION

Figure 1:
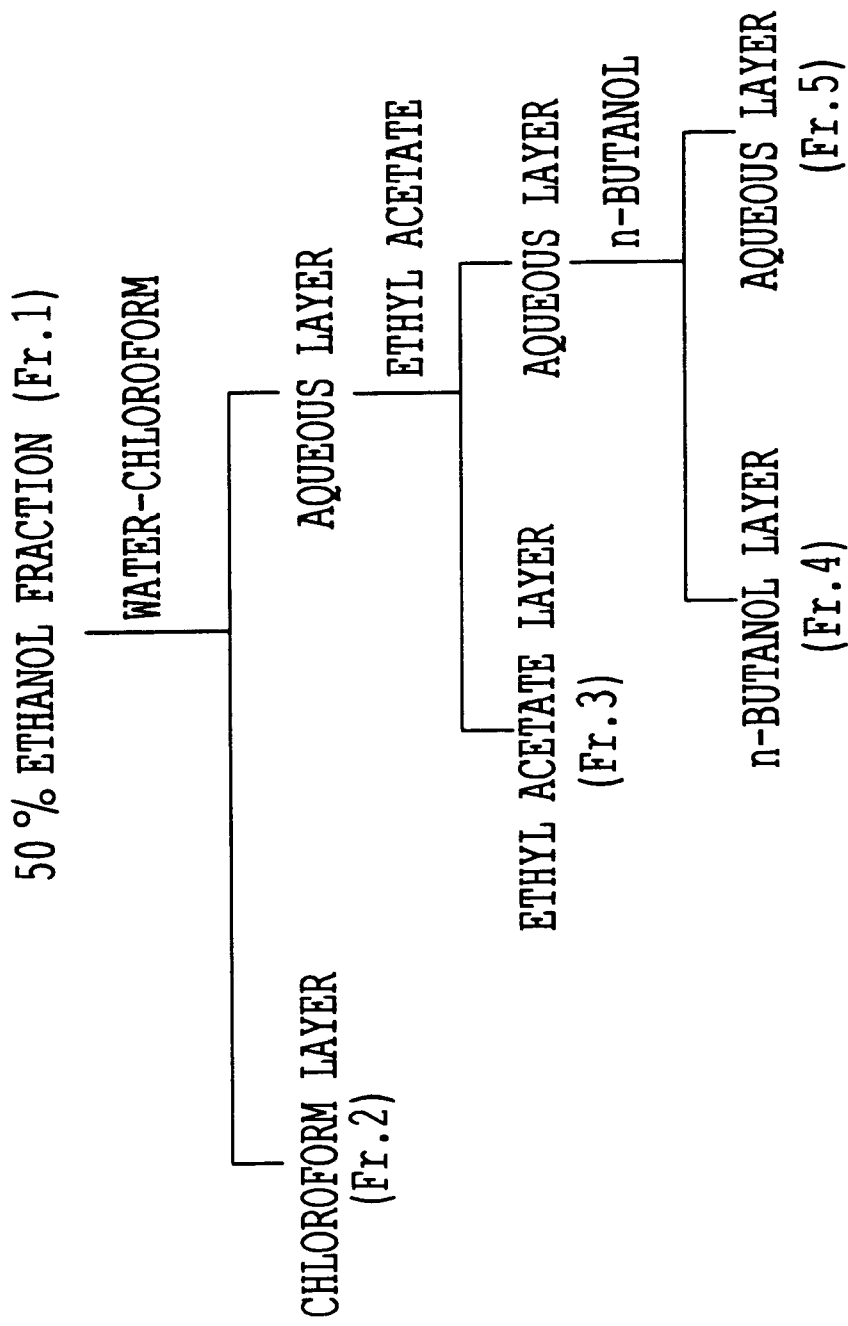
FIG. 1 is a flow chart showing an example of a method for the purification of strictinin.

Strictinin according to the invention is a compound represented by the following structural formula and, in addition to the said compound, a polyphenol which is a methylated derivative or a mixture thereof may be used in the present invention as well. Examples of the polyphenol are those where galloyl group, digalloyl group, trigalloyl group, hexahydroxyphenoyl group, 3-O-methylgalloyl group or 4-O-methylgalloyl group is introduced into at least one of the hydroxyl groups at C1 to C4 and C6 of glucose.

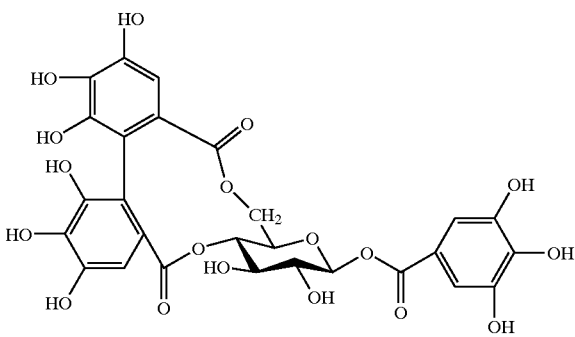

Tea (*Camellia sinensis*) has been drunk from ancient time and has been always taken for a long period and it has been noted that tea has no bad affection to human body but is a beverage with a very high safety. Accordingly, the tea leaf extract mainly comprising a polyphenol compound such as strictinin used in the invention can be accepted as being taken without anxiety.

The polyphenols such as strictinin used in the invention can be separated and collected from a polyphenol fraction obtained by an extraction of dried tea leaves such as "yabukita" tea leaves with an aqueous solvent. When the extract is utilized in and taken as food and/or beverage, cosmetics, etc. in its final stage, it is preferred from the standpoint of safety that water, ethanol or a mixture thereof is used as a solvent.

Although there is no particular limitation for the ratio (by weight) of the tea leaves to the solvent, the ratio from 5 to 100 parts of the solvent to 1 part of tea leaves is preferred. With regard to the temperature for the extraction, there is no particular limitation as well and, usually, the range of from the room temperature to the boiling point of the solvent under an atmospheric pressure is preferred in view of the operation. Time for the extraction is preferably within a range of from 10 minutes to 6 hours.

The tea leaf extract mainly comprising polyphenols such as strictinin used in the invention may be administered per se either as it is or after appropriately diluting with water or the like. It is also possible that it is made into a pharmaceutical preparation together with a commonly used pharmaceutical carrier. For example, the above-mentioned extract or the like can be made into a liquid preparation for oral use such as a syrup or made into a solid preparation for oral use such as tablets, capsules, granules or diluted powder after processing into extract, powder, etc. followed by compounding with a pharmaceutically acceptable carrier. With regard to the pharmaceutically acceptable carrier, various organic or inorganic carrier substances which have been commonly used as the materials for pharmaceutical preparations may be used and they are compounded as vehicles, lubricant, binder, disintegrator, etc. in a solid preparation or as solvent, excipient, suspender, binder, etc. in a liquid preparation. If necessary, additives for pharmaceutical preparations such as antiseptic, antioxidant, coloring agent, sweetener, etc. may be used as well.

Suitable examples of the vehicles or excipient are lactose, white sugar (sucrose), D-mannitol, starch, crystalline cellulose and light anhydrous silicic acid. Suitable examples of the lubricant are magnesium stearate, calcium stearate, talc and colloidal silica. Suitable examples of the binder are binding cellulose, white sugar, D-mannitol, dextrin, hydroxypropyl cellulose, hydroxypropyl methyl cellulose and polyvinylpyrrolidone.

Suitable examples of the disintegrator are polyethylene glycol, propylene glycol, D-mannitol, benzyl benzoate, ethanol, trisaminomethane, cholesterol, triethanolamine, sodium carbonate and sodium citrate. Suitable examples of the solvent are purified water, ethyl alcohol and propylene glycol. Suitable examples of the suspending agent are surface-active agent such as ethanolamine stearate, sodium laurylsulfate, laurylaminopropionic acid, lecithin, benzalkonium chloride, benzethonium chloride and glycerol monostearate and hydrophilic high-molecular compounds such as polyvinyl alcohol, polyvinylpyrrolidone, carboxymethyl cellulose, methyl cellulose, hydroxymethyl cellulose, hydroxyethyl cellulose and hydroxypropyl cellulose.

Suitable examples of the antiseptic are p-hydroxybenzoates, chlorobutanol, benzyl alcohol, phenethyl alcohol, dehydroacetic acid and sorbic acid. Suitable examples of the antioxidant are sulfites and ascorbic acid.

The tea leaf extract mainly comprising polyphenols such as strictinin used in the present invention may be administered either as it is or the extract is made into dry extract or powder to make in a form of food and/or beverage. It is compounded with a commonly used material for food and/or beverage and a carrier or the like which is acceptable for the manufacture of food and/or beverage and examples of the beverage are mixed tea drink, carbonate beverage, fruit beverage, lactic acid bacteria beverage, sport beverage and soybean milk. Examples of confectionery are biscuit, chocolate, candy, chewing gum, snack cake, fried cake, western unbaked cake, Japanese cake, ice cream and jelly cake. Examples of food are bread, noodle; processed soy bean products such as soybean curd; milk products such as yogurt and butter; meat products such as ham and sausage; omelet; fish meat paste products such as kamaboko; condiments such as sauce, dressing, mayonnaise and fish flour; and meals such as curry, stew, hamburger and soup. They can be prepared by conventional methods.

Examples of the carrier which is acceptable in the manufacture of food and/or beverage are sweeteners such as sugar, glucose, fructose, isomerized liquid sugar, fructooligosaccharide, aspartame, sorbitol and stevia; coloring agents such as red cabbage dye, grape rind dye, elderberry dye, caramel, gardenia dye, corn dye, saffron dye and carotene; preservatives such as decomposed pectin, benzoic acid, sorbic acid, p-hydroxybenzoates and potassium sorbate; pastes such as sodium alginate, propylene glycol alginate, calcium cellulose glycolate and sodium cellulose glycolate; antioxidants such as L-ascorbic acid, tocopherol, erythorbic acid and rutin; coloring former such as ferrous sulfate, sodium nitrite and potassium nitrite; bleaching agents such as sodium hydrogen sulfite and potassium metabisulfite; quality maintaining agents such as propylene glycol; quality improving agents such as L-cysteine hydrochloride and calcium stearyllactate; inflating agents such as ammonium chloride, potassium hydrogen d-tartrate, ammonium carbonate, potassium carbonate, sodium hydrogen carbonate and alum; emulsifiers such as lecithin, sphingolipid, vegetable sterol, soybean saponin, sodium alginate, propylene glycol alginate, sodium caseinate, glycerol fatty acid ester, sucrose fatty acid ester and sorbitan fatty acid ester; emulsion stabilizers such as sodium chondroitin sulfate; flavoring agents such as lemon oil, eucalyptus oil, peppermint oil, vanilla extract, orange oil, garlic oil, ethyl acetoacetate, anisaldehyde, ethylvanillin, cinnamic acid, citronellyl acetate, citral, vanillin, butyl butyrate and esters; enrichers such as L-ascorbic acid, L-asparagine, L-alanine, inositol, L-glutamine, carotene, tocopherol, vitamin A, folic acid, iron citrate, heme iron and non-calcined calcium; improving agents for wheat flour such as benzoyl peroxide, ammonium persulfate and chlorine dioxide; bactericides such as bleaching powder, hydrogen peroxide and hypochlorous acid; base materials for chewing gum such as methyl acetylricinolate, ester gum, vinyl acetate resin, polyisobutylene and polybutene; adherence preventers such as D-mannitol; binders such as sodium acidic pyrophosphate, potassium pyrophosphate and sodium pyrophosphate; acidic taste agents such as adipic acid, citric acid, gluconic acid, succinic acid, D-tartaric acid, lactic acid and DL-malic acid; seasonings such as fish/shellfish extract, yeast extract, sea tangle extract, soybean sauce, tomato puree, meat extract, mirin (Japanese sweet rice wine), fruit puree, dried bonito, sodium L-aspartate, DL-alanine, L-arginine, L-glutamate, disodium 5'-inosinate, trisodium citrate, L-glutamic acid, sodium L-glutamate, succinic acid, L-tartaric acid and sodium lactate.

The tea leaf extract mainly comprising polyphenols such as strictinin according to the invention is diluted with water or the like, concentrated or made into powder or granules followed by making into pharmaceutical preparation together with known pharmaceutical carriers to give the dosage forms such as aerosol, liquid, extract, suspension, emulsion, ointment, poultice, liniment or lotion. Or, if necessary, aqueous component, surface-active agent, oily component, solubilizer, moisturizer, powder component, alcohol, pH adjusting agent, antiseptic, antioxidant, thickener, dye, pigment, perfume, etc. which are known to be used for cosmetics, semi-pharmaceuticals and pharmaceuticals are appropriately selected whereupon a desired form is prepared.

As an externally applied agent for the skin, it is possible to make into the form of, for example, lotion, gel, emulsion, ointment, etc. whereby it is possible to provide as a cosmetic agent in various forms including cosmetic lotions such as softening cosmetic agent and astringent cosmetic lotion; creams such as emollient cream, moisture cream and massage cream; milky lotions such as emollient milky lotion, nourishing milky lotion and cleansing milky lotion; make-up cosmetics such as face-washing agent, skin cleanser, foundation, eye color, cheek color and lipstick; hair cosmetics such as shampoo, rinse, hair treatment, hair cream, hair dressing, hair tonic, pilatory and hair growing agent; bathing agents such as bath oil, bath salt and foam bath; etc.

In the present invention, polyphenols such as strictinin may be used in an appropriate amount taking the object for use, etc. into consideration and, for example, in the case of antiallergic agent or anti-inflammatory agent, the amount of 5–100 mg/kg or, preferably, 10–50 mg/kg per day is appropriate.

When used in food and/or beverage, polyphenols such as strictinin which are effective ingredients are used within a range of 5–100 mg/kg or, preferably, 10–50 mg/kg per day. Similarly, in the case of cosmetics, polyphenols such as strictinin which are effective ingredients are used within a range of 5–100 mg/kg or, preferably, 10–50 mg/kg per day.

Incidentally, in any of the above cases, the amount may be used once daily or by dividing into several times a day.

Antiallergic agent and anti-inflammatory agent of the present invention and cosmetics containing the same are effective for prevention, suppression or mitigation of inflammation and the symptoms caused by allergic reaction. In addition, since such pharmaceutical agents contain polyphenol compounds such as strictinin contained in tea as effective ingredients, safety is high and no toxic adverse action is noted to human body even by administration for a long period whereby they can be daily taken. Further, when food and/or beverage containing a tea extract mainly comprising polyphenol compounds such as strictinin is daily taken, it is useful for prevention and mitigation of the symptoms by allergic reaction.

EXAMPLES

In order to illustrate the invention in detail, representative Examples and Experimental Examples will be given as hereunder although the invention is not limited thereto.

Experimental Example 1

Extraction of Polyphenol Fraction from Various Tea Leaves (Tea Leaf Extract).

Tea leaves (100 g) dried with microwave were extracted with 50% methanol and the extracted fraction was extracted with 30% chloroform. Its aqueous phase was further extracted with ethyl acetate and the ethyl acetate layer after the extraction was fractionated using an ODS column. An example of the method for the purification of strictinin is shown in FIG. 1. The fractionated fractions were named Fr. 1 to 5, respectively. All of Fr. 1 to 5 were once freeze-dried and then Fr. 1 to 2, Fr. 3 to 4 and Fr. 5 were dissolved in water, 0.2% DMSO and 0.1% DMSO, respectively so that each fraction was made 1 mg/mL.

Experimental Example 2

Identification of Active Fractions.

Each of Fr. 1 to 5 in Experimental Example 1 was evaluated for its antiallergic action in vitro by a method for the expression of a transcript of an IgE heavy chain germline transcript which was to investigate the suppression of IgE production in human B cells (IgE class switch suppression). This is a method utilizing the fact that, when human B cells are stimulated by IL-4 to induce the production of IgE, a transcription is started from the upstream intron corresponding to an ε region (Cε) in the constant domain gene of the Ig gene whereupon a transcript (CεGT: germline transcript) is expressed and, after that, a class switch of IgE is resulted by a DNA recombination. CεGT is an RNA which is always expressed before the IgE production is induced and the expressed amount of CεGT is proportional to the class switch amount of the IgE gene. Therefore, when the degree of expressed amount of CεGT is detected, it is possible to estimate the IgE class switch amount.

A method for the expression of an IgE heavy chain germline transcript was carried out according to the following procedures.

Human B cell line DND 39 (available from Hayashibara Biochemical Laboratory) was prepared into $1\times10^5$ cells/mL and stimulated by adding IL-4 thereto to make the final concentration 25 U/mL. At that time, each of Fr. 1 to 5 prepared in Experimental Example 1 in a concentration of 10 μg/mL was added together with IL-4.

In the meanwhile, IL-4 (final concentration: 25 U/mL) and 2 ng/mL of a transforming growth factor β (TGF-beta; manufactured by Peprotech) were added to the above human cell line and the mixture was used as a positive control for suppressing the expression of CεGT.

They were incubated for 48 hours and centrifuged (300×g, 37° C.) to collect the cells and the total RNA was extracted with 1 mL of a reagent for collection and extraction of RNA (trade name: Trizol; manufactured by Gibco BRL).

Then, a cDNA library was prepared according to the following procedure. First, concentration of the extracted total RNA was measured by an absorptiometer, a portion of 10 μg was taken in a 0.6 mL tube and water was added thereto to make 11.8 μL. To this were added each 1.0 L of a 0.5 μg/μL oligo dT primer and a 20 μM CεGT antisense primer. The tube was incubated at 70° C. for 10 minutes and quickly cooled in ice for 10 minutes and annealed to anneal mRNA, oligo dT primer and CεGT antisense primer. This was mixed with 2.0 μL of an RNase-free 10 mM dNTP (manufactured by Amersham), 4.0 μL of 5×buffer attached to an MMLV-reverse transcriptase (manufactured by Amersham), 0.1 μL of an RNase inhibitor (manufactured by Takara Shuzo) and 0.1 μL (final concentration: 20–200 units/tube) of an MMLV-reverse transcriptase. The mixture was incubated at 37° C. for 1 hour to synthesize cDNA. The synthesized cDNA was amplified by a PCR. Sense and antisense primers were prepared based upon a base sequence of human GAPDH and CεGT registered at the Gene Bank. The structures are shown in the Sequence Listing. Thus, a CεGT sense primer, a CεGT antisense primer, a human GAPDH sense primer and a human GAPDH antisense primer are shown in SEQ ID NO:1, NO:2, NO:3 and NO:4, respectively.

CεGT-DNA was amplified using the said primer by a polymerase chain reaction (PCR) method. As a template for the PCR, 1 μL of an original solution of cDNA was used and, for the detection of CεGT, 0.8 μL of 10 mM dNTP, 0.5 μL of sense primer, 0.5 μL of antisense primer, 0.1 μL of AmpliTaq Gold (manufactured by Perkin Elmer) and 1 μL of 10×buffer attached to the AmpliTaq Gold were mixed and distilled water was added thereto to make the total volume 10 μL.

For the detection of GAPDH, 0.8 μL of 10 mM dNTP, 1 μL of $MgCl_2$, 0.5 μL of sense primer, 0.5 μL of antisense primer, 0.1 μL of Taq polymerase (manufactured by Fermentas) and 1 μL of 10×Taq buffer attached to the Taq polymerase were mixed and distilled water was added thereto to make the total volume 10 μL.

A PCR was carried out using a GeneAmp PCR System 2400 (manufactured by Perkin Elmer) and the condition therefor was as follows. Thus, for the detection of CεGT, a cycle of 95° C. for 30 seconds, 60° C. for 30 seconds and 72° C. for 30 seconds was conducted for 15 cycles and, finally, a reaction was carried out at 72° C. for 7 minutes. For the detection of GAPDH, a cycle of 95° C. for 30 seconds, 60° C. for 30 seconds and 72° C. for 30 seconds was conducted for 10 cycles and, finally, a reaction was carried out at 72° C. for 7 minutes. After that, the resulting PCR product was subjected to an electrophoresis using an agarose gel for separation (concentration: 1%; manufactured by Sawadi Technology). After completion of the electrophoresis, it was transcribed to a plus-charged Nylon membrane (manufactured by Amersham) (a southern transfer).

After that, a hybridization was carried out on the Nylon membrane to which the migrated pattern was transcribed using an oligo DNA fluorolabeled with CεGT-DNA which was amplified for 15 times in the above-mentioned PCR [which was prepared in such a manner that an oligonucleotide (SEQ ID NO:5 of the Sequence Listing) was picked out from a region pinched by the above-mentioned sense and antisense primers used for the PCR based on a base sequence of human CεGT and then the oligonucleotide is applied to an oligo labeling kit (manufactured by Amersham)] as a probe. After the hybridization, a reaction with CDP-Star (Amersham) which was a fluorescence detecting agent was carried out and the expressed amount of CεGT was measured from the resulting fluorescence intensity. FIG. 2 shows an influence of each fraction on CεGT inducible expression by IL-4 in the human B cell line DND 39. In the drawing, GAPDH means glyceraldehyde-3-phosphodehydrogenase and □ shows a control.

As will be apparent from FIG. 2, the expressed amount of CεGT was suppressed in the fraction of Fr. 3 as compared with other fractions. From that fact, it was found that an active component was available in the fraction of Fr. 3 and, after that, the fraction was finely fractionated using an ODS column whereupon one of the fractions was found to be a fraction containing strictinin only.

Experimental Example 3

Measurement of Antiallergic Activity in Human B Cell line.

Figure 3A:
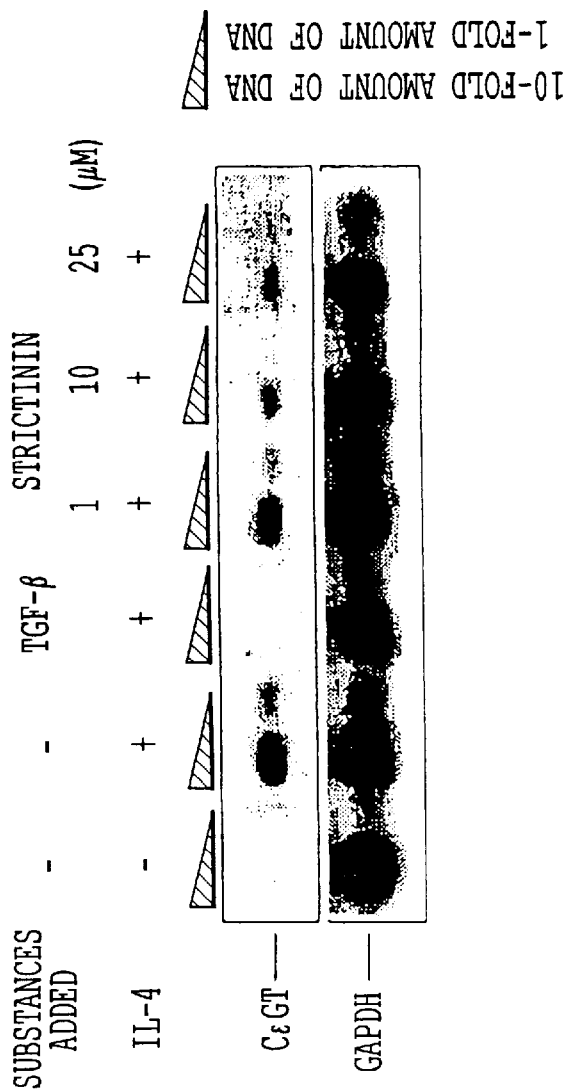
FIG. 3 shows an influence of strictinin on a CεGT-inducible expression by IL-4 in human B cell line DND 39.
Figure 3B:
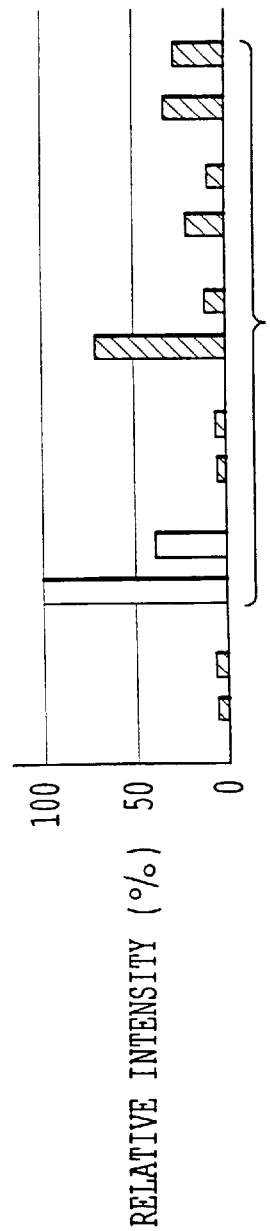

Strictinin which was identified as an active component in Experimental Example 2 was used for measuring the antiallergic activity in human B cell line according to the same way as in the method for the expression of an IgE heavy chain germline transcript mentioned in Experimental Example2. Incidentally, strictinin was added at the same time with IL-4. The adding concentrations of strictinin were 1, 10 and 25 μM. FIG. 3 shows an influence of strictinin on the CεGT inducible expression by IL-4 in the human cell line DND 39. In the drawing, GAPDH shows glyceraldehyde-3-phosphodehydrogenase and □ shows a control.

As shown in FIG. 3, it was apparent that, in the human B cell line, strictinin strongly suppressed the IgE class switch by addition of IL-4. Since IgE is an immunoglobulin deeply participating in the allergic reaction, the fact that IgE class switch is suppressed means that antiallergic activity is available.

Experimental Example 4

Measurement of Antiallergic Activity in Human Peripheral Blood Lymphocytes.

Figure 4A:
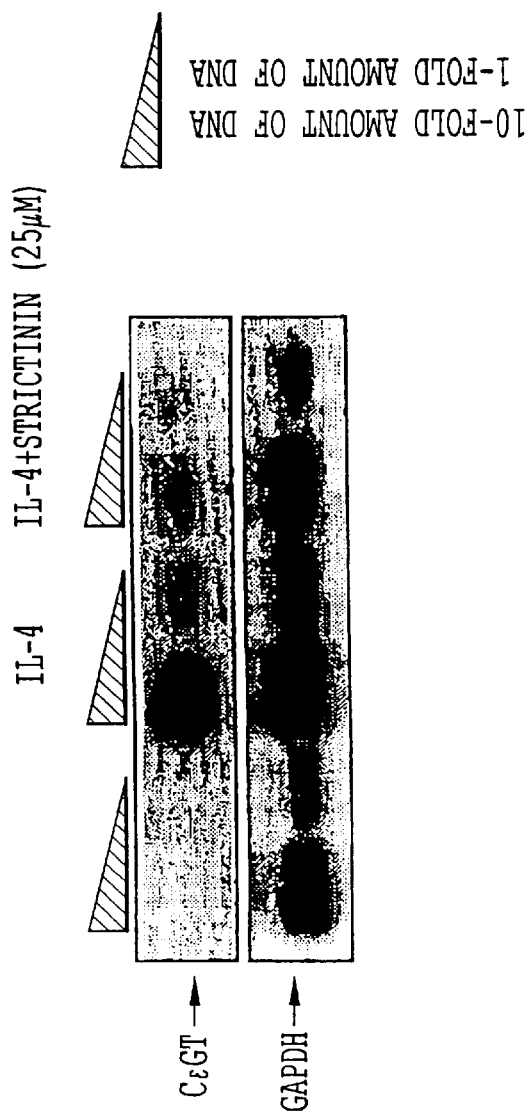
FIG. 4 shows an influence of strictinin on a CεGT-inducible expression by IL-4 in human peripheral blood lymphocytes.
Figure 4B:
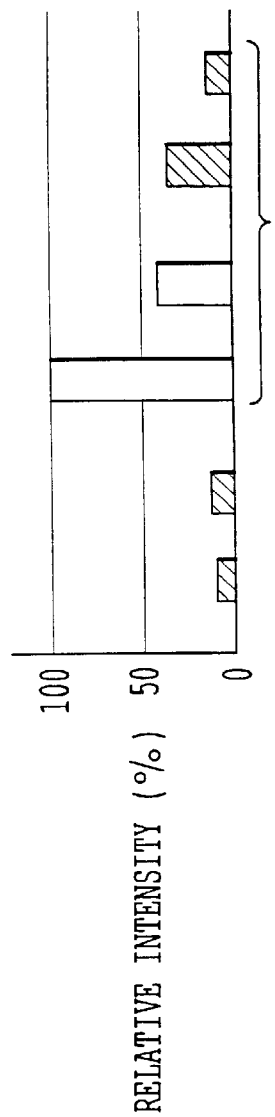

Human peripheral blood normal cells (monocytes; separated from the blood which was collected from a healthy human volunteer) was used instead of the human B cell line DND 39 of Experimental Example 3 and an antiallergic activity was measured by the same way as in the method for the expression of an IgE heavy chain germline transcript mentioned in Experimental Example 2. Like in Experimental Example 2, strictinin was added at the same time with IL-4. Incidentally, the adding concentration of strictinin was made 25 $\mu$M. FIG. 4 shows an influence of strictinin on the C$\epsilon$GT inducible expression by IL-4 in the human peripheral blood lymphocytes. In the drawing, GAPDH shows glyceraldehyde-3-phosphodehydrogenase and □ shows a control.

As shown in FIG. 4, strictinin strongly suppressed the IgE class switch by addition of IL-4 in the human peripheral blood lymphocytes and was noted to have an antiallergic activity.

Example 1

Manufacture of Candy.

Candy was manufactured by a conventional method using the following materials. As to a polyphenol fraction containing strictinin, etc., Fr. 3 in Experimental Example 1 was used (the same one was used in all the following Examples as well).

| | |
|---|---|
| Powdery sorbitol | 97.7 g |
| Perfume | 0.2 g |
| Sorbitol seed | 0.05 g |
| Polyphenol fraction containing strictinin, etc. | 0.05 g |
| Total | 100 g |

Example 2

Manufacture of Chewing Gum.

Chewing gum was manufactured by a conventional method using the following materials.

| | |
|---|---|
| Gum base | 20 g |
| Calcium carbonate | 2 g |
| Stevioside | 0.1 g |
| Polyphenol fraction containing strictinin, etc. | 0.05 g |
| Lactose | 76.85 g |
| Perfume | 1 g |
| Total | 100 g |

Example 3

Manufacture of Bathing Agent.

A bathing agent containing a tea leaf extract mainly comprising strictinin was manufactured by a conventional method using the following materials.

| | |
|---|---|
| Dry sodium sulfate | 53 g |
| Sodium hydrogen carbonate | 40 g |
| Light calcium carbonate | 1 g |
| Silicic acid anhydride | 1 g |
| Polyphenol fraction containing strictinin | 5 g |
| Perfume | a little |
| Pigment | a little |
| Total | 100 g |

---

What is claimed is:

1. A food that is supplemented with purified strictinin or a methylated derivative thereof, wherein said food is formulated to be used in an amount of 5–100 mg/kg of strictinin or a methylated derivative of strictinin per day.

2. The food of claim 1 that is selected from the group consisting of a confectionery, a bread, a noodle, a meat product, a fishmeat paste product, an omelet, a processed soybean product, a milk product and a condiment.

3. The food of claim 1 that is selected from the group consisting of chocolate, candy and chewing gum.

4. The food of claim 1 that is selected from the group consisting of bread, a noodle, biscuit, snack cake, fried cake, western unbaked cake, Japanese cake, and jelly cake.

5. The food of claim 1 that is a meat product.

6. The food of claim 1 that is a milk product.

7. The food of claim 1 that is ice cream, yogurt or butter.

8. The food of claim 1 that is selected from the group consisting of a sauce, dressing, mayonnaise, and fish flour.

9. The food of claim 1 that is selected from the group consisting of curry, stew, soup and hamburger.

10. A beverage that is supplemented with purified strictinin or a methylated derivative thereof, wherein said beverage is formulated to be used in an amount of 5–100 mg/kg of strictinin or a methylated derivative of strictinin per day.

11. The beverage of claim 10 selected from the group consisting of a mixed tea beverage, a carbonated beverage, a fruit beverage, a beverage containing lactic acid bacteria, soybean milk and a sports beverage.

12. A cosmetic supplemented with purified strictinin, wherein said cosmetic is formulated to be used in an amount of 5–100 mg/kg of strictinin or a methylated derivative of strictinin per day.

13. The cosmetic of claim 12 selected from the group consisting of a lotion, gel, emulsion, ointment, cream, cleanser, make up cosmetic, hair cosmetic and bathing agent.

14. A method for supplementing a cosmetic comprising:
adding purified strictinin or a methylated derivative of strictinin to a cosmetic, wherein said cosmetic is formulated to be used in an amount of 5–100 mg/kg of strictinin or a methylated derivative of strictinin per day.

15. The method of claim 14, comprising adding strictinin to said cosmetic.

16. The method of claim 14, comprising adding a methylated derivative of strictinin to said cosmetic.

17. A method for supplementing a food or a beverage comprising:
adding purified strictinin or a methylated derivative of strictinin to a food or beverage, wherein said food or beverage is formulated to be used in an amount of 5–100 mg/kg of strictinin or a methylated derivative of strictinin per day.

18. The method of claim 17, comprising adding strictinin to said food or beverage.

19. The method of claim 17, comprising adding a methylated derivative of strictinin to said food or beverage.

20. The food of claim 1 that is supplemented with strictinin.

21. The food of claim 1 that is supplemented with a methylated derivative of strictinin.

22. The food of claim 1 that is formulated to be used in an amount of 10–50 mg/kg of strictinin or a methylated derivative of strictinin per day.

23. The beverage of claim 10 that is supplemented with strictinin.

24. The beverage of claim 10 that is supplemented with a methylated derivative of strictinin.

25. The beverage of claim 10 that is formulated to be used in an amount of 10–50 mg/kg of strictinin or a methylated derivative of strictinin per day.

26. The cosmetic of claim 12 that is supplemented with strictinin.

27. The cosmetic of claim 12 that is supplemented with a methylated derivative of strictinin.

28. The cosmetic of claim 12 that is formulated to be used in an amount of 10–50 mg/kg of strictinin or a methylated derivative of strictinin per day.

* * * * *